US012029907B2

(12) United States Patent
Kahana et al.

(10) Patent No.: US 12,029,907 B2
(45) Date of Patent: Jul. 9, 2024

(54) METHOD AND APPARATUS FOR IMPROVING COGNITIVE PERFORMANCE THROUGH CORTICAL STIMULATION

(71) Applicant: The Trustees of the University of Pennsylvania, Philadelphia, PA (US)

(72) Inventors: Michael Kahana, Merion Station, PA (US); Daniel Sutton Rizzuto, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 473 days.

(21) Appl. No.: 16/318,738

(22) PCT Filed: Jul. 19, 2017

(86) PCT No.: PCT/US2017/042759
§ 371 (c)(1),
(2) Date: Jan. 18, 2019

(87) PCT Pub. No.: WO2018/017655
PCT Pub. Date: Jan. 25, 2018

(65) Prior Publication Data

US 2019/0282815 A1 Sep. 19, 2019

Related U.S. Application Data

(60) Provisional application No. 62/365,538, filed on Jul. 22, 2016.

(51) Int. Cl.
*A61N 1/36* (2006.01)
*A61B 5/00* (2006.01)
(Continued)

(52) U.S. Cl.
CPC ............ *A61N 1/36092* (2013.01); *A61B 5/24* (2021.01); *A61B 5/291* (2021.01); *A61B 5/369* (2021.01);
(Continued)

(58) Field of Classification Search
CPC ..... A61B 5/04; A61B 5/04001; A61B 5/0476; A61B 5/0478; A61N 1/0531;
(Continued)

(56) References Cited

U.S. PATENT DOCUMENTS 7,299,096 B2 11/2007 Balzer et al.
8,150,524 B2 4/2012 Maschino et al.
(Continued)

FOREIGN PATENT DOCUMENTS

WO WO-2004052449 A1 * 6/2004 ............... A61N 1/08
WO 2015149170 A1 10/2015
(Continued)

OTHER PUBLICATIONS

International Search Report dated Sep. 27, 2017 for International Patent Application No. PCT/US2017/042759, 2 pages.
(Continued)

*Primary Examiner* — Allen Porter
*Assistant Examiner* — Adreanne A. Arnold
(74) *Attorney, Agent, or Firm* — Morgan, Lewis & Bockius LLP

(57) ABSTRACT

Methods and apparatus for improving cognitive function within a human. The invention utilizes a neurostimulation device, such as a signal generator, to affect tissue elements at a lateral temporal lobe of the human brain. The implanted device delivers treatment therapy to thereby improve cognitive function by the human. A sensor may be used to detect various characteristics of cognition. A microprocessor algo-
(Continued)

B
523
522
Device
16 rithm may then analyze the output from the sensor to regulate delivery of the stimulation therapy.

8 Claims, 4 Drawing Sheets

(51) Int. Cl.
*A61B 5/24* (2021.01)
*A61B 5/291* (2021.01)
*A61B 5/369* (2021.01)
*A61N 1/05* (2006.01)

(52) U.S. Cl.
CPC ....... *A61N 1/0531* (2013.01); *A61N 1/36082* (2013.01); *A61N 1/36139* (2013.01); *A61N 1/36171* (2013.01); *A61N 1/36175* (2013.01); *A61B 5/4064* (2013.01); *A61B 5/4088* (2013.01); *A61B 5/4836* (2013.01); *A61B 5/686* (2013.01); *A61N 1/36157* (2013.01)

(58) Field of Classification Search
CPC ............ A61N 1/36082; A61N 1/36139; A61N 1/36171; A61N 1/36092
See application file for complete search history.

(56) References Cited

U.S. PATENT DOCUMENTS

| | | | | |
|---|---|---|---|---|
| 2005/0033378 | A1* | 2/2005 | Sheffield | A61N 1/36082 607/45 |
| 2007/0055320 | A1* | 3/2007 | Weinand | A61N 1/36064 607/45 |
| 2010/0030211 | A1* | 2/2010 | Davalos | A61B 18/1477 606/41 |
| 2010/0145176 | A1* | 6/2010 | Himes | A61B 5/0002 600/545 |
| 2012/0016430 | A1* | 1/2012 | Lozano | A61K 45/06 607/3 |
| 2014/0025133 | A1 | 1/2014 | Lozano | |
| 2017/0249853 | A1* | 8/2017 | Weiss | G09B 5/00 |

FOREIGN PATENT DOCUMENTS

| | | | | |
|---|---|---|---|---|
| WO | WO-2015149170 | A1 * | 10/2015 | A61B 5/0008 |
| WO | 2015191628 | A1 | 12/2015 | |
| WO | 2018017655 | A1 | 1/2018 | |

OTHER PUBLICATIONS

Written Opinion dated Sep. 27, 2017 for International Patent Application No. PCT/US2017/042759, 4 pp.

Supplementary European Search Report dated Dec. 11, 2019 for International Patent Application No. PCT/US2017/042759, 7 pages.

Jacobs et al (2016) Direct Electrical Stimulation of the Human Entorhinal Region and Hippocampus Impairs Memory: http://dx.doi.org/10.1016/j.neuron.2016.10.062.

Ezzyat et al (2018) Closed-loop stimulation of temporal cortex rescues functional networks and improves memory: https://doi.org/10.1038/s41467-017-02753-0.

Kahana et al (2021) Biomarker-guided neuromodulation aids memory in traumatic brain injury: https://doi.org/10.1101/2021.05.18.21256980.

* cited by examiner

METHOD AND APPARATUS FOR IMPROVING COGNITIVE PERFORMANCE THROUGH CORTICAL STIMULATION

CROSS-REFERENCE TO RELATED APPLICATION

This application is a U.S. National Stage of International Patent Application No. PCT/US2017/042759, filed Jul. 19, 2017, which claims the benefit of priority to U.S. Provisional Application No. 62/365,538 filed Jul. 22, 2016, the entirety of which are incorporated herein by reference.

GOVERNMENT SUPPORT

The present invention was made with Government support under Grant No. N66001-14-2-4032 awarded by Space and Naval Warfare Systems Center, Pacific. The Government has certain rights in the invention.

BACKGROUND

The present invention relates to techniques for providing treatment therapy to improve cognitive function through stimulation of a human brain.

Cognitive disorders are a common type of neurological disorders. For example, dementia is form of impaired cognition caused by brain dysfunction. The hallmark of most forms of dementia is the disruption of memory performance. Among the several conditions labeled as dementia, the most common are Alzheimer's disease (AD) and mild cognitive impairment (MCI), which is a pre-clinical form of Alzheimer's disease. MCI is an intermediate state between normal aging and dementia and is characterized by acquired cognitive deficits, without significant decline in functional activities of daily living. Subjects with MCI and the initial phase of Alzheimer's disease originally present with a predominant deficit in cognitive function. In more advanced stages of Alzheimer's disease, impairment in additional cognitive domains culminates with a significant decline in quality of life and the inability to perform usual daily activities.

Alzheimer's disease is one of the most common cognitive disorders in humans and has an exponentially increasing incidence. Although the defining characteristic of Alzheimer's disease is cognitive impairment, it is often accompanied by mood and behavioral symptoms such as depression, anxiety, irritability, inappropriate behavior, sleep disturbance, psychosis, and agitation. Neuro-imaging and genetic testing have aided in the identification of individuals at increased risk for dementia. However, the measurement of change in cognitive and functional status in, for example, MCI remains challenging because it requires instruments that are more sensitive and specific than those considered adequate for research in dementia. Accordingly, no treatment exists that adequately prevents or cures Alzheimer's disease or MCI.

Alzheimer's disease and MCI are already a public health problem of enormous proportions. It is estimated that 5 million people currently suffer with Alzheimer's disease in the United States. This figure is likely underestimated due to the high number of unrecognized and undiagnosed patients in the community. By the year 2050, Alzheimer's is projected to affect 14 million people. Moreover, because the prevalence of Alzheimer's disease doubles every 5 years after age 65, the impact of the disease on society tends to increase with the growth of the elderly population. The annual cost in the United States of AD alone is approximately $100 billion.

There is currently no effective treatment for the memory loss and other cognitive deficits presented by patients with dementia, particularly Alzheimer's disease. Treating Alzheimer's disease tends to be more challenging than other neurological disorders because Alzheimer's largely affects a geriatric population. Oral medications including Acetylcholinesterase inhibitors and cholinergic agents are the mainstay treatment for this condition. Nevertheless, the outcome with these agents is modest and tends to decline as the disease progresses. Other agents, such as nonsteroidal anti-inflammatory drugs, corticosteroids, COX-2 inhibitors, estrogen, and antioxidants, have also been tried with poor results. Neurotrophic factors (molecules that increase survival and growth of neurons in laboratory experiments) have been recently used clinically for Alzheimer's disease. Because these agents are proteins, they are inactive with oral administration and cannot cross the blood-brain barrier when administered systemically. When infused intraventricularly in three patients with Alzheimer's disease, nerve growth factor (NGF) increased cerebral nicotine binding. However, this compound had only modest clinical effects and was associated with back pain and weight loss that were reversible with the cessation of treatment.

Alternative routes of neurotrophic factor administration are currently being studied. Gene therapy and small neurotrophic molecules that can penetrate the blood-brain barrier (AIT-082) are possible methods for drug delivery. Moreover, treatment strategies against beta-amyloid protein accumulation and plaque formation including immunotherapies with vaccines are other possible methods. However, clinical data is still lacking for any of these alternative methods for treating cognitive disorders.

Most aspects of cognitive function involve temporal lobe structures. Amnesic syndromes have been described after the disruption of the hippocampus, amygdala, fornix, mammilary bodies, anterior nucleus of the thalamus, rhinal cortex, parahippocampal cortex, and temporal neocortex. These structures are mainly involved with declarative memory, which comprises the memory for facts, events, spatial location, recognition of forms, significance of data processed, among others. However, to date, no interventions at the temporal lobe have been successful in improving cognitive function.

It is therefore desirable to provide a technique for preventing or treating cognitive disorders such as Alzheimer's disease and, more broadly, to improve cognitive function in patients or healthy individuals.

SUMMARY

In one embodiment, there is provided a method for treating a human cognitive disorder or enhancing normal cognition using a neurostimulator device including signal generator and a lead having a proximal end coupled to the signal generator and a distal portion having at least one electrode, the method comprising: (a) positioning a stimulation portion of the at least one electrode in or on the lateral temporal lobe of a brain; (b) coupling the proximal end of the lead implanted electrode to the signal generator; and (c) treating the cognitive disorder or enhancing normal cognition by operating the signal generator to deliver stimulation to the lateral temporal lobe of the brain via the electrode.

BRIEF DESCRIPTION OF THE SEVERAL VIEWS OF THE DRAWINGS

The following detailed description of embodiments of the invention will be better understood when read in conjunction with the appended drawings of an exemplary embodiment. It should be understood, however, that the invention is not limited to the precise arrangements and instrumentalities shown.

In the drawings.

DETAILED DESCRIPTION

Figure 1:
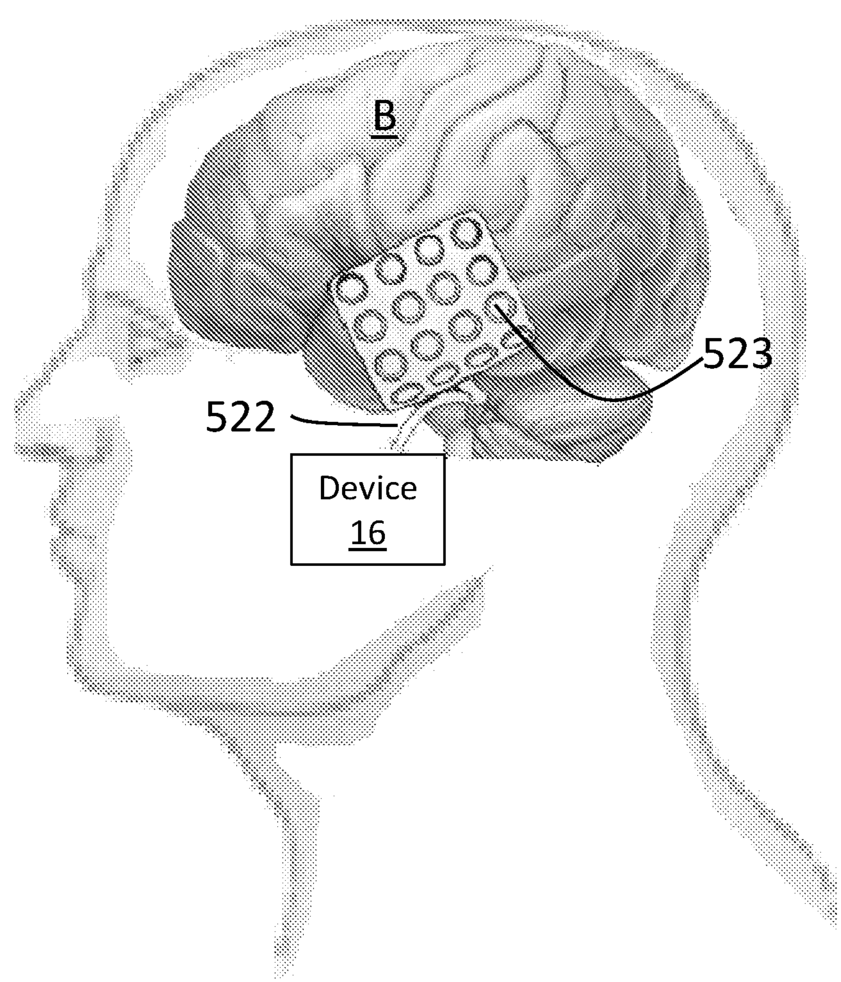
FIG. 1 is a diagrammatic illustration of an electrode implanted in a brain according to an embodiment of the present invention and a signal generator coupled to the electrode.

The invention discloses techniques for delivering treatment therapy to the lateral temporal lobe of a human brain to improve cognitive function.

The temporal lobe is one of the four major lobes of the cerebral cortex in the brain of mammals. It is located beneath the lateral fissure on both cerebral hemispheres of the mammalian brain and is involved in processing sensory input into derived meanings for the appropriate retention of memories, language comprehension, and emotion association.

The temporal lobe is divided into two areas, the lateral temporal lobe and the medial temporal lobe. The lateral temporal lobe is the portion of the temporal lobe located furthest from the midline of the mammal, while the medial temporal lobe is the portion of the temporal lobe positioned at or near the midline of the mammal. Each area of the temporal lobe includes subregions. The lateral temporal lobe subregions include superior temporal gyms, middle temporal gyms, inferior temporal gyms, temporopolar cortex and fusiform cortex. The medial temporal lobe includes hippocampus, entorhinal cortex, parahippocampal cortex, perirhinal cortex and amygdala.

Conventional treatment therapy delivery systems focused on stimulating the medial temporal lobe, rather than the lateral temporal lobe, because studies have shown that damage to the medial temporal lobe results in profound memory deficits. Unsurprisingly, researchers and clinicians focused on the medial temporal lobe, based on an assumption that because damage to the medial temporal lobe resulted in memory deficits, stimulation to the medial temporal lobe should result in memory improvements.

However, the applicant has discovered that these treatment therapies are not as effective as the embodiments of the invention, described herein. The applicant has recognized that even though the medial temporal lobe plays a significant role in memory, successful memory encoding and retrieval results from connectivity and interaction between the medial temporal lobe and other portions of the brain, such as the lateral temporal lobe. The applicant also recognized that, because of this connectivity, stimulation of a first portion of the brain can induce a response in a second portion of the brain, providing an overall synergistic response to electrical stimulus as compared to stimulation of the second portion of the brain directly. Recognizing the synergistic effects of stimulation on different areas of the brain, the applicant studied stimulation on different areas of the brain associated with cognitive function to determine the areas that provided a synergistic response, and thereby improved cognitive function.

As a result, the applicant has discovered that cognitive function can be improved through delivery of treatment therapy to the lateral temporal lobe, rather than the medial temporal lobe because stimulation of the lateral temporal lobe can induce a response in the medial temporal lobe as well. Accordingly, embodiments of the invention incorporate electrical stimulation techniques to directly or indirectly influence tissue elements at or within the lateral temporal lobe. One or more electrodes can be positioned at or near the lateral temporal lobe of the brain (or, optionally implanted in the lateral temporal lobe of the brain) so that the stimulation portions lie within or in communication with predetermined portions of the brain. The electrical stimulation influences the lateral temporal lobe to achieve the desired result.

The techniques of the present invention are suitable for use within any neurostimulation medical device. In some embodiments, the present invention is implemented within an implantable neurostimulator system, however, those skilled in the art will appreciate that the present invention may be implemented generally within any implantable medical device system or non-implantable medical device system.

In addition, the present invention may be embodied in various forms to analyze and treat cognitive disorders. Such disorders include, for example without limitation, Alzheimer's disease, MCI, dementia, amnesia and memory disorders as can occur after injury, trauma, stroke, cranial irradiation, and in the context of genetic, congenital, infectious, autoimmune, toxic (drugs and alcohol), nutritional (vitamin deficiencies) metabolic, inflammatory, neurodegenerative neoplastic or idiopathic processes involving the brain. Some additional specific disorders where the therapy of the invention may be useful include: amnestic syndromes, Wernicke-Korsakoff and Korsakoff syndromes, Herpes encephalitis, severe hypoxia, vascular disorders, head injury, transient global amnesia, global amnesia, epileptic amnesia, cerebral palsy, autism, mental retardation and attention deficit and hyperactivity disorders.

Referring to FIG. 1, a neurostimulator device 16 made in accordance with an embodiment may be operable to stimulate the lateral temporal lobe of a brain (B) of a mammal (e.g., human, the term "human" being used herein for convenience). A lead 522 is positioned to stimulate a lateral temporal lobe in a brain (B). One or more external programmers (not shown) may be utilized to program and/or communicate bi-directionally with the neurostimulator device 16.

As shown, the distal end of the lead 522 terminates at an electrode 523 positioned at the lateral temporal lobe, or alternatively, implanted at the lateral temporal lobe of the brain by conventional stereotactic surgical techniques. The electrode 523 is in electrical communication with device 16 through e.g., the lead 522, where a proximal end of the lead 522 is coupled to the device 16.

In some embodiments, the lead 522 may be divided into a two (or more) leads that are implanted into the brain bilaterally at different hemispheres of the brain (B). In some embodiments, each of the two leads includes one or more corresponding electrodes positioned at or implanted in the lateral temporal lobe on one hemisphere of the brain (B).

The device 16 may be operated to deliver electrical stimulation to the lateral temporal lobe via electrode 523 to thereby improve cognitive function in the human or treat a cognitive disorder. The device 16 can be provided subclavicularly or in the skull of the human, among other locations. The particular stimulation delivered may be performed by selecting amplitude, pulse width and frequency of stimulation delivered by the electrode.

In some embodiments, the pulse frequency is selected from: up to about 300 Hertz, between about 50 and about 250 Hertz, and between about 100 and about 200 Hertz. In some embodiments, the pulse width is selected to be about 200 μ-seconds. As used herein, the term "about" may refer to + or −10% of the value referenced. For example, "about 9" is understood to encompass 8.2 and 9.9.

In some embodiments, the pulse amplitude is selected from: up to about 5 milliamps, and up to about 2 milliamps for pulse amplitude.

In some embodiments, the pulse width is selected from: up to about 500 μ-seconds, and between about 100 to about 300 μ-seconds.

Figure 2:
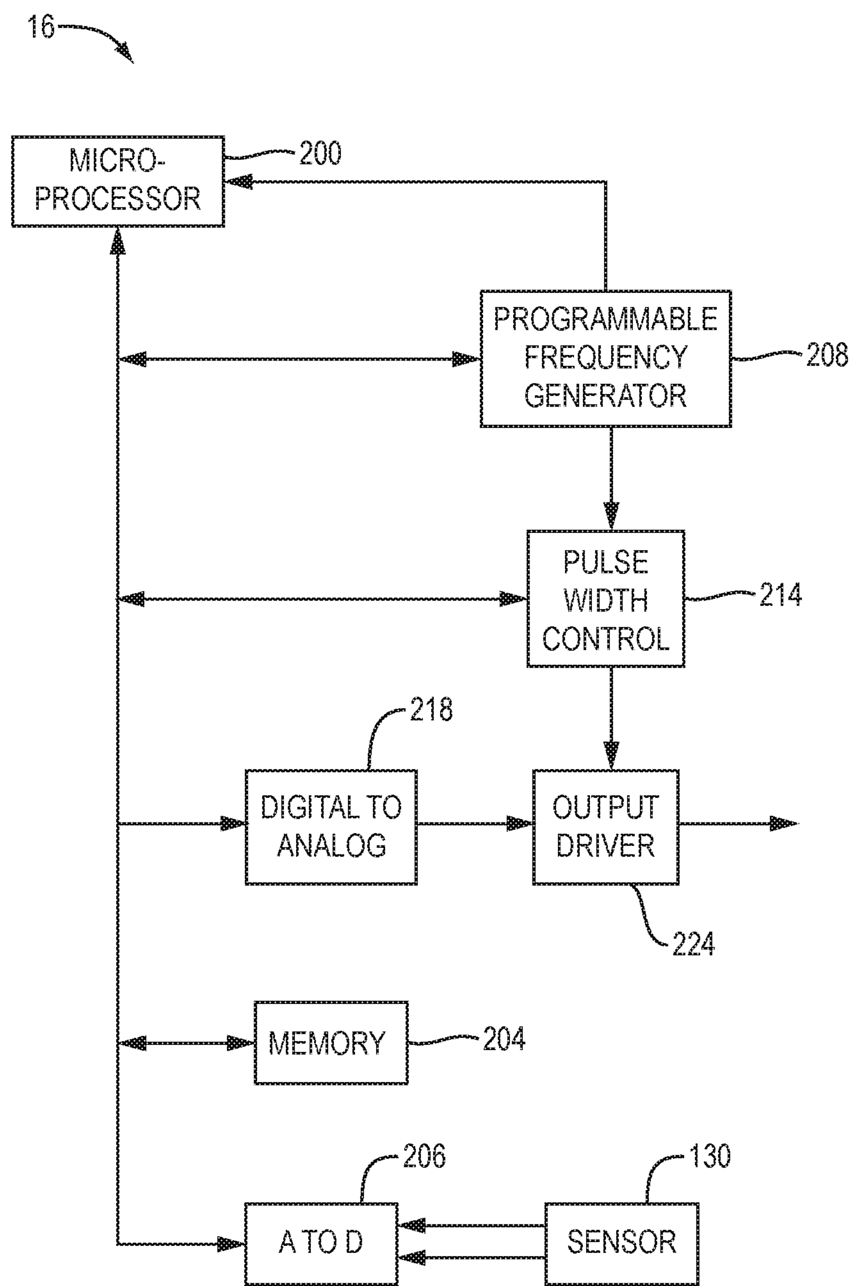
FIG. 2 is a schematic block diagram of a microprocessor and related circuitry of an implantable medical device for use with the present invention.

Referring to FIG. 2, the overall components of the device 16 are illustrated. The stimulus pulse frequency is controlled by programming a value to a programmable frequency generator 208 using bus 202. The programmable frequency generator 208 provides an interrupt signal to microprocessor 200 through an interrupt line when each stimulus pulse is to be generated. The amplitude for each stimulus pulse is programmed to a digital to analog converter 218 using bus 202. The analog output is conveyed through a conductor to an output driver circuit 224 to control stimulus amplitude.

Microprocessor 200 also programs a pulse width control module 214 using bus 202. The pulse width control provides an enabling pulse of duration equal to the pulse width via a conductor. Pulses with the selected characteristics are then delivered from device 16 to electrode 523 through lead 522 to the lateral temporal lobe of the brain (B) (as shown in FIG. 1).

In some embodiments, before stimulation, a clinician can program certain key parameters into the memory of the implanted device via telemetry. These parameters may be updated subsequently as needed.

The embodiments of the present invention shown above are open-loop systems. The microcomputer algorithm programmed by the clinician sets the stimulation parameters of device 16. This algorithm may change the parameter values over time but does so independent of any changes in symptoms the patient may be experiencing. Alternatively, a closed-loop system discussed below which incorporate a sensor 130 to detect biomarkers and provide feedback could be used to provide enhanced results. Sensor 130 can be used with a closed loop feedback system in order to automatically determine the level of electrical stimulation necessary to achieve the desired level of improved cognitive function. In a closed-loop embodiment, microprocessor 200 executes an algorithm in order to provide stimulation with closed loop feedback control. Such an algorithm may analyze a sensed signal and deliver the electrical treatment therapy based on the sensed signal falling within or outside predetermined values or windows.

For example, in one embodiment, the patient may engage in a specified cognitive task and wherein the system measures one or more characteristics to determine if the sensed levels are at expected thresholds. If one or more of the sensed characteristics are outside a predetermined threshold, the system may initiate and/or regulate the treatment therapy to thereby enhance cognitive function.

In one embodiment, the system may be continuously providing closed-loop feedback control. In another embodiment, the system may operate in closed-loop feedback control based on a time of day (e.g., during hours that the patient is awake) or based on a cognitive task (e.g., when the patient is working). In yet another embodiment, the system may be switchable between open-loop and closed-loop by operator control.

In another embodiment, the stimulation delivery could be applied before, after and/or during the performance of a memory, cognitive or motor learning task to facilitate the acquisition of learning or consolidation of the task and in so doing, accelerate the rate of memory acquisition and learning and enhance its magnitude. For example, the stimulation delivery may be provided before, during, or after periods when the patient is learning a new language or playing a new instrument. Such therapy may be useful during the encoding, consolidation and/or retrieval phases of memory. The stimulation delivery could occur before, after or simultaneously to the memory, cognitive or motor skill task.

Referring back to FIG. 2, the system may optionally utilize closed-loop feedback control having an analog to digital converter 206 coupled to sensor 130. Output of the A-to-D converter 206 is connected to microprocessor 200 through peripheral bus 202 including address, data and control lines. Microprocessor 200 processes sensor data in different ways depending on the type of transducer in use and regulates delivery, via a control algorithm, of electrical stimulation delivery based on the sensed signal. For example, when the signal on sensor 130 exceeds a level programmed by the clinician and stored in a memory 204, increasing amounts of stimulation may be applied through an output driver 224. In the case of electrical stimulation, a parameter of the stimulation may be adjusted such as amplitude, pulse width and/or frequency.

Parameters which could be sensed include the activity of single neurons as detected with microelectrode recording techniques, local field potentials, event related potentials, for example in response to a memory task or sensory stimulus and electroencephalogram or electrocorticogram. In another embodiment, an electro-physiological characteristic of the cognitive function may be sensed. The information contained within the local field potential, including amplitude, power, phase, phase-amplitude coupling, signal to noise ratio, and correlated activity between multiple sensors could be used to deliver therapies on a contingency basis in a closed loop system. Moreover, treatment therapy delivered may be immediate or delayed, diurnal, constant or intermittent depending on contingencies as defined by the closed loop system.

Results

In one study performed using embodiments of the invention described herein, the applicant found that stimulation of the lateral temporal lobe produced a significant enhancement of memory performance. In this study, a subject was presented with a list of 12 words, one at a time on a computer screen. Stimulation was administered during some of the list presentations. The subject participated in six total sessions of testing. In three of those sessions, the left middle temporal gyms (Left MTG Stim condition) was stimulated, and in the other three sessions, the left perirhinal cortex (PRC Stim condition) was stimulated. All sessions included some lists where stimulation was not administered at all (NoStim condition).

Figure 3:
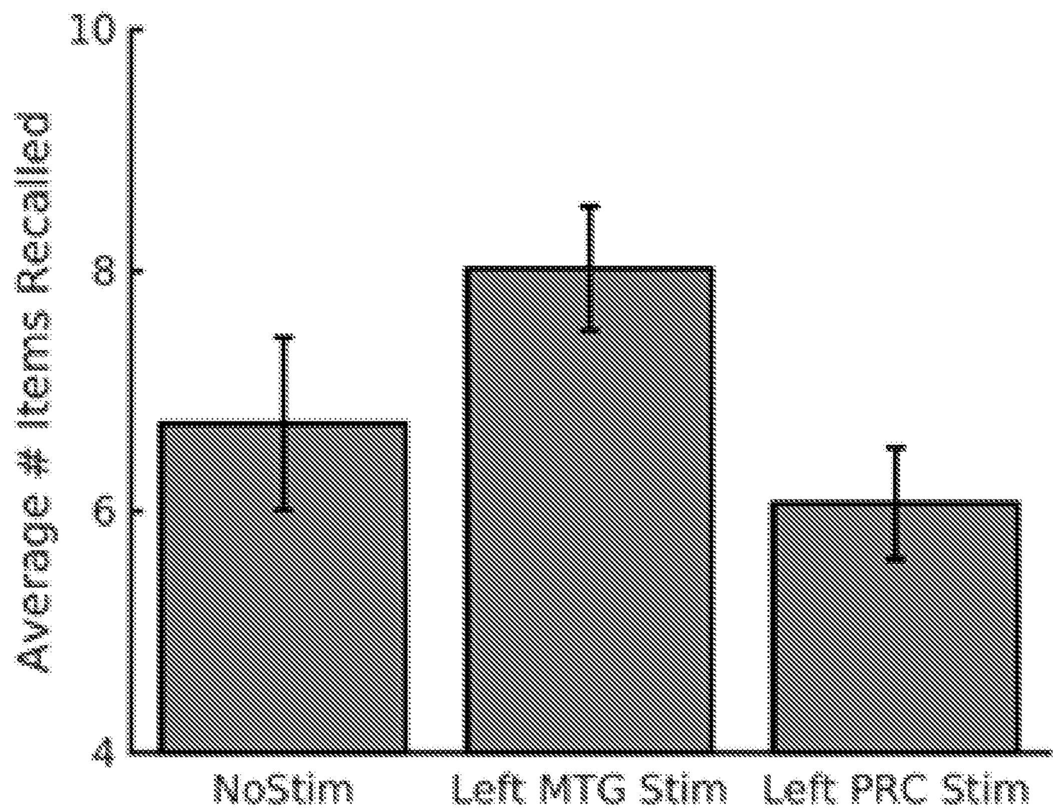
FIG. 3 is a chart illustrating the average number of items recalled during three different conditions, each using different stimulation parameters.

The patient remembered significantly more words if stimulated in Left MTG during list presentation, compared to all non-stimulated (NoStim) lists collected across the six sessions (see FIG. 3). Within the three MTG stimulation sessions, memory for stimulated lists was higher than for NoStim lists (66.8% vs. 53.3%, $P<0.001$). In contrast to the results in MTG, it was observed that there was a significant decrease in memory performance due to Left PRC stimulation (50.6% vs. 58.9%, $P<0.05$).

Figure 4:
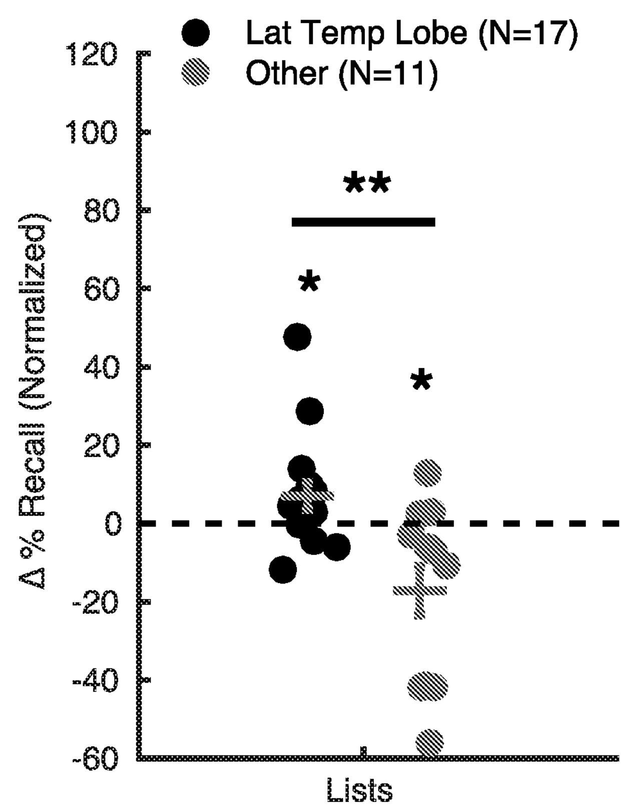
FIG. 4 is a chart illustrating the recall performance of subjects undergoing stimulation of either lateral temporal cortex or other brain regions.

The previous finding was subsequently replicated in a larger cohort of 28 subjects, 17 of whom received stimulation of lateral temporal cortex and 11 of whom received stimulation in other brain areas (FIG. 4). Subjects receiving lateral temporal cortex stimulation during word encoding (black dots) had significantly better memory recall performance than subjects receiving stimulation of other brain areas (grey dots; $p<0.05$).

In at least one embodiment, there is included one or more computers having one or more processors and memory (e.g., one or more nonvolatile storage devices). In some embodiments, memory or computer readable storage medium of memory stores programs, modules and data structures, or a subset thereof for a processor to control and run the various systems and methods disclosed herein. In one embodiment, a non-transitory computer readable storage medium having stored thereon computer-executable instructions which, when executed by a processor, perform one or more of the methods disclosed herein.

It will be appreciated by those skilled in the art that changes could be made to the exemplary embodiments shown and described herein without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

What is claimed is:

1. A method for treating a human cognitive disorder or enhancing normal cognition using a neurostimulator device including a signal generator and a lead having a proximal end coupled to the signal generator and a distal portion having at least one electrode, the method comprising:

(a) implanting a sensor only within a left middle temporal gyrus of a brain;

(b) implanting a stimulation portion of the at least one electrode within only the left middle temporal gyrus of a brain;

(c) coupling the at least one electrode to the signal generator using the lead;

(d) sensing an electrophysiological characteristic indicative of normal, enhanced, or impaired cognition only at the left middle temporal gyrus with the sensor;

(e) determining an appropriate level of electrical stimulation based on the sensed electrophysiological characteristic; and (f) treating the cognitive disorder or enhancing normal cognition by operating the signal generator to deliver stimulation at the appropriate level only to the left middle temporal gyrus of the brain via the electrode.

2. The method of claim 1, wherein (f) is performed in relation to a learning task.

3. The method of claim 2, wherein the learning task is selected from the group consisting of a memory task, a cognitive task, and a motor task.

4. The method of claim 1, wherein (f) comprises selecting amplitude, pulse width, and frequency of stimulation by the electrode.

5. The method of claim 1, wherein (f) comprises operating the signal generator to pulse at a pulse width of up to 500 μ seconds.

6. The method of claim 1, wherein (d) comprises detecting an electrophysiological characteristic selected from the group consisting of activity of single neurons, local field potentials, event related potentials, an electroencephalogram, and an electrocorticogram.

7. The method of claim 1, wherein (f) comprises adjusting at least one parameter of the stimulation, the parameter being selected from the group consisting of amplitude, pulse width, and frequency.

8. The method of claim 1, wherein said cognitive disorder is selected from the group: Alzheimer's disease, MCI, dementia, amnesia, and memory disorders as can occur after injury, trauma, stroke, cranial irradiation, and in the context of genetic, congenital, infectious, autoimmune, toxic (drugs and alcohol), nutritional (vitamin deficiencies), metabolic, inflammatory, neurodegenerative neoplastic or idiopathic processes involving the brain, amnestic syndromes, Wernicke-Korsakoff and Korsakoff syndromes, Herpes encephalitis, severe hypoxia, vascular disorders, head injury, transient global amnesia, global amnesia, epileptic amnesia, cerebral palsy, autism, mental retardation, and attention deficit and hyperactivity disorders.

* * * * *

UNITED STATES PATENT AND TRADEMARK OFFICE

CERTIFICATE OF CORRECTION

PATENT NO. : 12,029,907 B2
APPLICATION NO. : 16/318738
DATED : July 9, 2024
INVENTOR(S) : Michael Kahana and Daniel Sutton Rizzuto It is certified that error appears in the above-identified patent and that said Letters Patent is hereby corrected as shown below:

In the Specification

On Column 1, Lines 17-20, after the heading "GOVERNMENT SUPPORT":
"The present invention was made with Government support under Grant No. N66001-14-2-4032 awarded by Space and Naval Warfare Systems Center, Pacific. The Government has certain rights in the invention."

Should read:
--This invention was made with government support under N66001-14-2-4032 awarded by the Defense Advanced Research Projects Agency. The government has certain rights in the invention.--

On Column 3, Lines 43-46:
"The lateral temporal lobe subregions include superior temporal gyms, middle temporal gyms, inferior temporal gyms, temporopolar cortex and fusiform cortex."

Should read:
--The lateral temporal lobe subregions include superior temporal gyrus, middle temporal gyrus, inferior temporal gyrus, temporopolar cortex and fusiform cortex.--

On Column 6, Lines 65-67, and Column 7, Line 1:
"In three of those sessions, the left middle temporal gyms (Left MTG Stim condition) was stimulated, and in the other three sessions, the left perirhinal cortex (PRC Stim condition) was stimulated."

Should read:
--In three of those sessions, the left middle temporal gyrus (Left MTG Stim condition) was stimulated, and in the other three sessions, the left perirhinal cortex (PRC Stim condition) was stimulated.--

Signed and Sealed this
Fifteenth Day of October, 2024

Katherine Kelly Vidal

Katherine Kelly Vidal
*Director of the United States Patent and Trademark Office*